United States Patent [19]
Ananthapadmanabhan et al.

[11] Patent Number: 4,743,550
[45] Date of Patent: May 10, 1988

[54] METHOD FOR IMPROVING THE PARTITION COEFFICIENT IN ENZYME-CONTAINING SYSTEMS HAVING AT LEAST TWO PHASES

[75] Inventors: Kavssery P. Ananthapadmanabhan, Spring Valley, N.Y.; Errol D. Goddard, Haworth, N.J.

[73] Assignee: Union Carbide Corporation, Danbury, Conn.

[21] Appl. No.: 799,329

[22] Filed: Nov. 12, 1985

Related U.S. Application Data

[63] Continuation-in-part of Ser. No. 728,241, Apr. 29, 1985.

[51] Int. Cl.$^4$ .................. C12N 9/52; C12N 9/00; C12N 9/50; C12N 9/54; C12N 9/56
[52] U.S. Cl. .................. 435/220; 435/183; 435/219; 435/221; 435/222; 435/816
[58] Field of Search .................. 435/183, 219–230, 435/814, 816

[56] References Cited

U.S. PATENT DOCUMENTS

| | | | |
|---|---|---|---|
| 3,695,999 | 10/1972 | Forgione | 435/816 UX |
| 4,144,130 | 3/1979 | Kula et al. | 435/210 X |
| 4,343,735 | 8/1982 | Menge et al. | 260/112 R |
| 4,451,487 | 5/1984 | Vetter et al. | 435/183 |
| 4,572,897 | 2/1986 | Amotz et al. | 435/177 |

OTHER PUBLICATIONS

S. D. Flanagan, Affinity Phase Partitioning, *Receptor Biochem. Methodol.*, 2, 15–44 (1984).
G. Johansson and M. Andersson, Parameters Determining Affinity Partitioning of Yeast Enzymes Using Polymer-Bound Trizine Dye Ligands, *J. Chrom.*, 303, 39–51 (1984).
V. P. Shanbhag and G. Johansson, Interaction of Human Serum Albumin with Fatty Acids, *Eur. J. Biochem.*, 93, 363–367 (1979).
G. Birkenmeier, B. Tschechonien, and G. Koppers- chlager, Affinity Chromatography and Affinity Partition of Human Serum Pre-Albumin Using Immobilized Remazol Yellow GGL *FEBS Letters*, 174, 162–166 (1984).
C. Axelsson and V. P. Shanbhag, Histone-Hydrocarbon Interaction, Partition of Histones in Aqueous Two-Phase Systems Containing Poly(Ethylene Glycol)-Bound Hydrocarbons, *Eur. J. Biochem.*, 71, 419–423 (1976).
G. Johansson, The effect of Poly(Ethylene Glycol) Esters on the Partition of Proteins and Fragmented Membranes in Aqueous Biphasic Systems, *Bioch. Biophys. Acta*, 451, 517–529 (1976).
G. Johansson and V. P. Shanbhag, Affinity Partitioning of Proteins in Aqueous Two-Phase Systems Containing Polymer-Bound Fatty Acids, *J. Chrom.*, 284 63–72 (1984).
G. Johansson, Comparison of two Aqueous Biphasic Systems Used for the Separation of Biological Material, *J. Chrom.*, 150, 63–71 (1978).
G. Johansson, studies on Aqueous Dextran-Poly(Ethylene Glycol) Two-Phase Systems Containing Charged Poly(Ethylene Glycol) *Biochim. Biophys. Acta*, 222, 381–389 (1970).
S. D. Flanagan and S. H. Barondes, A Method for Purification of Proteins Using Specific Polymer-Ligands in Aqueous Polymer Two-Phase Systems, *J. Biol. Chem.*, 250, 1484–1489 (1975).

*Primary Examiner*—Lionel M. Shapiro
*Attorney, Agent, or Firm*—Steven H. Flynn

[57] ABSTRACT

A process for the recovery of enzymes from an aqueous system having at least two aqueous phases wherein the partition coefficient with respect to an enzyme may be improved through the addition of organo-compatible, compounds having anionic functionality, such as polyacrylic acid, polyvinyl sulfonate and sodium dodecylsulfate.

36 Claims, No Drawings

METHOD FOR IMPROVING THE PARTITION COEFFICIENT IN ENZYME-CONTAINING SYSTEMS HAVING AT LEAST TWO PHASES

This application is a continuation-in-part of U.S. Ser. No. 728,241, filed Apr. 29, 1985.

This invention relates to a process for the recovery of enzymes from solution through the use of an aqueous system having at least two aqueous phases to which has been added an effective amount of an organo-compatible compound which acts to enhance the concentration of the enzyme in one phase of the system. In particularly advantageous aspects, the instant invention provides a method for the recovery of alkaline protease in a polyethylene/inorganic-salt, two phase aqueous system wherein the partition coefficient of said system with respect to alkaline protease approaches infinity, thereby allowing complete recovery of the enzyme in the polyethylene glycol phase of the system.

BACKGROUND OF THE INVENTION

Affinity Partitioning

The potential applications for biologically active proteins have greatly increased. Commercial implementation of this technology now frequently depends on the ability to isolate these substances at reasonable cost. Until recently, separation technology which could support industrial applications was limited to filtration and centrifugation. However, these techniques are extremely dependant upon particle size and therefore approach their limit of usefulness during the harvest of even small intact microorganisms. The problems encountered are therefore greatly increased during the attempted isolation of intracellular components from ruptured cells where component size is, of course, greatly reduced.

The process of affinity partitioning using two phase aqueous systems has been suggested for some separations. Affinity partitioning basically involves the formation of multiple, distinct phases in a common solvent following the addition of materials, such as polymers, which produce immiscible phases when in solution and the selective affinity of a molecule for one phase over the other. The partition coefficient of a system is defined as the concentration of a specific material in the upper phase divided by its concentration in the lower phase of the system. It therefore describes the ability of a system to selectively concentrate a given material in one phase of the system. Aqueous two phase systems have been known since the late nineteenth century from the work of Beijerinck who published his findings regarding aqueous phase formation with agar and gelatin. As it is not dependant upon particle size as are conventional techniques such as filtration and centrifugation, affinity partitioning offers the potential of improved recovery of cellular components in industrial scale recoveries. The use of affinity partitioning in the isolation of enzymes from other cellular matter is disclosed in U.S. Pat. No. 4,144,130. Affinity partitioning technology has further been employed to date in the recovery of interferon (U.S. Pat. No. 4,343,735), the isolation of human coagulation factors VII and VIIa (U.S. Pat. No. 4,470,969) and the isolation of deoxyribonucleic acid (U.S. Pat. No. 4,207,200).

Alkaline Protease

Alkaline proteases are members of a class of enzymes which demonstrate peak proteolytic activity under neutral to alkaline conditions.

Alkaline proteases are known to possess excellent cleansing performance against proteinaceous substances found, for example, in clothing stains, especially when employed in the presence of a cleansing agent, such as a detergent, under alkaline conditions. Proteases are therefore attractive additives for cleansing formulations.

Unfortunately, typical two-phase systems such as those described hereinafter possesses alkaline protease partition coefficients which are too low to be employed in commercially viable recovery processes, due to, for instance, the high volumes required by such processes to produce a given amount of enzyme. Of course, increasing the coefficient increases the commercial potential of the system.

The applicants have therefore sought to provide through the present invention an improved method for isolation and recovery of an alkaline protease by improving the partition coefficient of an aqueous system having at least two phases through the addition of specific amounts of an additional compound, such as polyacrylic acid, to the system.

The enzyme produced through this process has been found to possess a significant level of its original catalytic activity.

SUMMARY OF THE INVENTION

This invention relates to a process for the recovery of enzymes from solution through the use of an aqueous system having at least two aqueous phases to which has been added an effective amount of an organo-compatible compound which acts to enhance the concentration of the enzyme in one phase of the system. In particularly advantageous aspects, the instant invention provides a method for the recovery of alkaline protease in a polyethylene/inorganic-salt, two phase aqueous system wherein the partition coefficient of said system with respect to alkaline protease approaches infinity, thereby allowing complete recovery of the enzyme in the polyethylene glycol phase of the system.

DETAILED DESCRIPTION OF THE INVENTION

While the methods of the invention may generally be applied in the isolation and stabilization of enzymes from an aqueous solution, the isolation of the most preferred enzyme, alkaline protease, shall be hereinafter described.

Commercially available alkaline proteases include Alkalase manufactured by Novo and the Milezyme APL series, manufactured by Miles Laboratories.

The procedures claimed herein are also applicable to the concentration of enzymes from aqueous solutions containing intact cells or fragments thereof. The claimed process may therefore be employed to isolate the enzyme from the broth produced by rupturing enzyme producing cells, thereby consolidating the usual process steps of sedimentation and enzyme isolation.

Enzymes, like other proteinaceous materials, may be electrochemically neutral or may exhibit an anionic or cationic character depending on the pH of its environment. The pH at which the enzyme is neutral is its isoelectric point, which can be determined by the absence of enzyme migration during gel electrophoresis. Typically, at a pH above the isoelectric point of a given enzyme, an enzyme will exhibit an anionic character. Below its isoelectric point, a cationic character will be exhibited. In the case of the preferred alkaline protease enzyme, its isoelectric point is about 7 to 9.

The additional compounds which may be employed in the practice of the instant invention are compounds having anionic functionality. This includes poly acids such as polyacrylic acid, carboxymethyl cellulose, polyvinyl sulfonic acid, polyphosphoric acid, polymethacrylic acids and other acidic copolymers such as the copolymer of maleic anhydride and vinyl methyl ether. These acids may of course, be used in the form of their salts. Other examples are alkali metal alkyl sulfates and sulfonates wherein the alkyl group contains from about 8 to 18, preferably 10 to 14 carbon atoms, and mixtures thereof. Sodium dodecyl sulfate, polyacrylic acid and polyvinyl sulfonate are preferred. If polyacrylic acid is employed, it preferably has an average molecular weight of between about 1,000 and 1,000,000. It may be added to the two-phase system in amounts ranging from about 0.0001 wt. % up to the point where precipitation of the enzyme occurs, which is about 0.2 wt. % based upon the weight of the system in the case of polyacrylic acid. Preferably, it is employed in amounts of from about 0.01 to 0.1 wt. % based upon the weight of the system. Similarly, sodium dodecyl sulfate and polyvinyl sulfonate may be present in amounts ranging from about 0.0001 to about 0.2 wt. % based upon the weight of the system, preferably from 0.01 to 0.01 wt. %. The polyvinyl sulfonate component preferably has an average molecular weight of between about 1000 and 1,000,000, most preferably about 10,000 to 200,000.

When employed in small quantities, the additional compounds have been found generally to decrease the partition coefficient of the enzyme/additional compound composition in a given system while their use in greater quantities tends to increase the partition coefficient.

In addition, the anionic functionality of the additional compound may be introduced into the system through the use of a modified phase-forming component. For example, a polyethylene glycol onto which has been grafted acrylate sulfate or sulfonate moieties may be employed. The grafted polymers should contain an amount of these anionic moieties such that their concentration in the system falls within the above-mentioned ranges for their use as independant components.

While not wishing to be bound to any specific reaction mechanism, it is believed that the additional compound (i.e., polyacrylic acid, etc.) interacts with the enzyme. It is further believed that the additional compound migrates into the phase due to either its attraction to the polyethylene glycol or its repulsion from the constituents of the bottom phase. Polyacrylic acid and polyvinyl sulfonate are believed to function in polyethylene glycol/water-soluble inorganic salt systems due to their attraction to polyethylene glycol while sodium dodecyl sulfate is thought to function due to its repulsion from the salt-containing lower phase and attraction to the upper phase. An increase in the partition coefficient through the use of additional compounds as herein described should therefore prevail in aqueous two-phase systems as long as the compound is neither repulsed from the upper phase nor attracted to the lower phase. For the purposes of this disclosure, a compound having either of these qualities will be said to be "organo-compatible". Alternately, that additional compound may be preferentially drawn to the polyethylene glycol phase. In the cases of polyacrylic acid and polyvinyl sulfonate, they are believed to interact with the enzyme present in the non-polyethylene glycol phase and enrich it in the polyethylene glycol phase due to their attraction to and affinity for polyethylene glycol. It is believed that both electrostatic forces and polar bonding are responsible for the attractions referred to immediately above, with their degree of importance depending upon the pH of the system. The polyacrylic acid-polyethylene glycol interaction is believed to be predominantly due to polar bonding at low pH with an increasing contribution due to ion-dipole interactions as pH rises. The interaction between the additional compound and the enzyme also needs to be considered. For example, when the pH of the system is below the isoelectric point of the enzyme, the enzyme exhibits a positive net charge. Polyacrylic acid, for example, at a pH above 4 exhibits the opposite net charge. Therefore, in the case of alkaline protease and a polyacrylic acid additive, at pH's of less than 7 and above about 5, electrostatic forces are believed to be responsible for much of the enzyme-additive attraction. At a pH at about and above the isoelectric point of the enzyme, electrostatic forces will tend to oppose enzyme-additive interaction. Instead, polar bonding is thought to be responsible for enzyme-additive attraction which is exhibited.

Examples of two phase aqueous systems which have been used in the isolation of alkaline protease are dextran/water-soluble copolymer of sucrose and epichlorohydrin, dextran/hydroxypropyl-dextran, polyethylene glycol/dextran sulfate, charged polyethylene glycol/dextran, dextran/polyethylene glycol, polypropylene glycol/methoxypolyethylene glycol, polypropyleneglycol/polyethylene glycol, polypropylene glycol/polyvinyl alcohol, polypropylene glycol/polyvinyl pyrrolidone, polypropylene glycol/hydroxypropyl-dextran, polypropylene glycol/dextran, polyethylene glycol/polyvinyl alcohol, polyethylene glycol/polyvinyl pyrrolidone, polyethylene glycol/water-soluble copolymer of sucrose and epichlorohydrin, polyethylene glycol/water-soluble starch, polyethylene glycol/glycogen, polyvinyl alcohol/methyl cellulose, polyvinyl alcohol/hydroxypropyl-dextran, polyvinyl alcohol/dextran, polyvinyl pyrrolidone/methyl cellulose, polyvinyl pyrolidone/dextran, methyl cellulose/hydroxypropyl dextran, methyl cellulose/dextran and ethylhydroxyethyl cellulose/dextran. These aqueous systems may also contain additional salts and organic solvents, adjuvants, etc.

Other aqueous systems which have been used are those composed of at least one polymer and one water soluble inorganic salt or organic solvent. The polymer may be chosen from those listed immediately above. Preferably the polymer may be polyethylene glycol, methoxypolyethylene glycol, ethoxypolyethylene glycol, polypropylene glycol, polyvinyl pyrrolidone or a water-soluble derivative thereof. Representative examples of water soluble inorganic salts are magnesium sulfate, potassium sulfate, sodium sulfate and sodium chloride. The organic solvents may include propylalcohol, glycerol and 2-butoxyethanol.

The systems can further contain additional materials including pH buffers such as tris(hydroxymethyl)-aminomethane, moropholino ethane sulfonate and citrate, which may be employed with saline.

Preferred are systems comprised of polyethylene glycol and water soluble inorganic salts. In this respect, more preferred is a system comprised of polyethylene glycol, methoxypolyethylene glycol or ethylene oxide/propylene oxide copolymers having an average molecular weight of about 1,000 to about 10,000, and sodium sulfate, wherein the sodium sulfate is present in a concentration of from about 1 to 40 wt. %, preferably about 5 to 25 wt. % based upon the weight of the total system.

The conditions present in the two-phase system are not critical except as noted below. Temperatures and pressures of the two phase system may vary widely; however they should be such that they do not denature the enzyme or diminish its potency beyond limits acceptable to its final application.

The pH of the system may generally be maintained at any level at which denaturation of the enzyme does not occur. Preferably, an alkaline protease-containing system should be maintained at a pH of greater than about 4 and less than 10, most preferably between about 5 and 8.

In addition to the aforementioned system components, the system may further comprise additional materials with the proviso that they do not adversely affect the potency of the protease to an undue degree.

The concentrated protease/additive composition may then be recovered from the system by conventional means, such as with the use of ion exchange resins. Alternately, it may be recovered through the formation of an enzyme/binder precipitate as shown and described in co-pending U.S. Ser. No. 728,241 which is hereby incorporated by reference. This method is advantageous in that (1) insoluble, enzyme-containing substances are produced, thereby allowing use of elementary recovery techniques such as filtration and centrifugation and (2) isolation of the enzyme-containing phase is not required.

As previously discussed, it is possible to alter the net electrical charge exhibited by an enzyme through variation of the pH of the aqueous system in which it is present. Therefore, an enzyme will typically exhibit an anionic character at pH's above its isoelectric point while exhibiting a cationic character below its isoelectric point. The enzyme will therefore exhibit an attraction to cationic and anionic binder materials under these respective conditions. The enzyme may further exhibit an attraction to binder materials while at its isoelectric point. Polar bonding is thought to explain this interaction. The process disclosed in U.S. Ser. No. 728,241 uses this attraction to form insoluble, enzyme-containing compositions through the addition of binder materials which interact with the enzyme.

The binder material may be any material which (1) is soluble in the aqueous media, (2) does not unduly degrade the potency of the enzyme to which it is bound and (3) effectively interacts with the enzyme to form an insoluble composition in the aqueous media which may later be disassociated to release the enzyme.

Anionic binders are those compounds having functional groups such as carboxylic acids. Examples of compounds which may be used as anionic binders are polycarboxylic acids such as polyacrylic acid and polymethacrylic acid. Other examples include polyvinyl sulfonate, polyvinyl sulfate, polyphosphoric acid, carboxymethylcellulose and the copolymer of maleic anhydride and vinyl methyl ether and mixtures thereof. Preferred for isolation of cationic enzyme is polyacrylic acid. Most preferred for this use is polyacrylic acid having a molecular weight of from about 1000 to 1,000,000. Polyacrylic acid is particularly preferred as it may be used in conjunction with enhancement of the partition coefficient of a two-phase system. That is, the amounts necessary to cause the formation of an enzyme-containing precipitate may be arrived at by simply adding polyacrylic acid to the amounts already present in solution from the initial process step wherein the partition coefficient was improved through its introduction in small quantities. Examples of cationic binders to be used with an enzyme above its isoelectric point, and therefore anionic in nature, are quaternized vinyl pyrrolidone/aminoethyl methacrylate copolymer, copolymer of adipic acid/dimethylaminohydroxy propyl diethylene triamine, poly(N,N-dimethyl-3,5 methylene piperidinium chloride, copolymer of acrylamide/beta methacryloxy ethyl trimethyl ammonium chloride, quaternized guar gum derivative, polyethylene imine, chitosan and a cationic cellulosic polymer marketed by Union Carbide Corporation, under the trademark of Polymer JR..

It has further been found that in addition to ionic binder materials, non-ionic materials may also be employed.

The association complexes which form at low pH's between the enzyme and polyacrylic acid or other polycarboxylic acids wherein most of the acid groups are not ionized, may also be viewed as this type of interaction. Examples of non-ionic or weakly acidic binders which may be employed in the isolation of an enzyme are phenolic resins such as "Bakelite BRL 3913" (manufactured by Union Carbide Corporation) and "Cascothen 511" (manufactured by Borden Company). Enzyme binder compositions may be formed with alkaline protease and either of these two non-ionic binders in aqueous and either of these two non-ionic binders in aqueous solutions having a pH of less than about 9, preferably less than 6.

Recovery of the insoluble enzyme/binder composition from solution may be accomplished through the use of conventional techniques, such as simple filtration or centrifugation.

The enzyme/binder composition may later be disassociated through exposure of the composition to a pH which promotes such dissociation. In the case where the binder is cationic, repulsion between a cationic enzyme and cationic binder will result in the disassociation of the composition. In the case of the compositions formed from cationic enzymes and anionic binders, the composition needs only be introduced into a solution having a pH above the isoelectric point of the bare enzyme. In the case of alkaline protease/polyacrylic acid binder composition, disassociation of the composition occurs under alkaline conditions, preferably at a pH above about 8.0. In the case of enzyme/binder compositions formed with binders of weaker acids, dissociation of the complex may be performed by exposure of the composition to solutions having a pH above about 10 if the binder becomes ionized at high pH. For example, in the case of either alkaline protease/"Bakelite" or alkaline protease/"Cascothen" compositions, dissociation of the compositions may be accomplished through exposure of the compositions to solutions having a pH above about 10.

In addition to the aforementioned compounds, the enzyme/binder composition may further comprise additional materials which similarly do not adversely affect the potency of the enzyme to an undue degree. Representative of these materials are polyethylene glycols, and surfactants such as sodium dodecylsulfate and sodium dodecylbenzene sulfonate. Preferred are polyethylene glycols having an average molecular weight of at least 1000, most preferably about 1,000 to 10,000. These materials may be present in amounts up to 50 wt. %, preferably up to 30 wt. %, based on the total weight of the enzyme/binder composition. These adjuvants may be added during formation of the enzyme/binder composition.

Formulation of the enzyme/binder composition may be accomplished through simple introduction of the binder into a solution containing an enzyme such as produced through the claimed coefficient-enhancing process, for a period adequate and accompanied with sufficient agitation or stirring to ensure adequate exposure of the composition components. The conditions present during formulation of the claimed enzyme/protease compositions are not critical except as noted. Temperatures and pressures should be such that they do not denature the enzyme or diminish its potency beyond limits acceptable to its final application.

The pH of the solution should be maintained at a level at which formation of the complex is promoted. This will, of course, vary with the enzyme and binder employed as explained above. In the case of the preferred alkaline protease/polyacrylic acid composition, the pH of the solution should be less than 6, preferably about 4 to 5.

The protease/binder composition can then be recovered from the mixing apparatus by conventional means, such as centrifugation or filtration. The composition may then be dried at a temperature less than that at which denaturation of the enzyme is encountered. This will, of course, depend upon the enzyme employed. In the case of the preferred composition, drying may be conducted at temperatures up to about 70 degrees C.

The following Examples are offered to demonstrate the improvement of the partition coefficient possible through use of the present invention.

All parts and percentages are by weight unless otherwise indicated. All temperature values are given in degrees Celsius.

EXAMPLES

Control

Approximately 1.0 g. of a liquid alkaline protease-containing composition manufactured by Miles Laboratories and marketed under the designation APL 440 were mixed with 554.56 g. of distilled water (hereinafter referred to as Solution A). According to its manufacturer, APL 440 possesses an activity of 440,000 DAPU/kg. A DAPU, or Detergent Alkaline Protease Unit, is defined as that activity which will liberate four nanomoles of tyrosine per minute under specified conditions. The method employed in the determination of this activity will be set forth below. The alkaline protease content of APL 440 is not known. For the purpose of the following experiments, APL 440 is assumed to be 100% pure and its activity is assumed to be 440,000 DAPU/kg. Solution A is therefore assumed to contain about 0.18 wt. % alkaline protease.

Determination of Activity

The assay is based on a proteolytic hydrolysis of a Hammerstein casein substrate in synthetic tap water over a period of 40 minutes at 40 degree Celsius. The tap water possesses a hardness of 269 ppm of calcium carbonate and a pH of 8.5. Unhydrolyzed substrate is precipitated with trichloroacetic acid and removed by centrifugation. The solubilized casein is then determined spectrophotometrically.

The following stock solutions were prepared.

Sol. 1. 500 ml. distilled water containing 12.6 g. of calcium chloride dihydrate.

Sol. 2. 500 ml. distilled water containing 7.0 g. of magnesium chloride.

Sol. 3. 500 ml. distilled water containing 10.5 g of anhydrous sodium bicarbonate. STW Synthetic tap water prepared by introducing 10 ml. of each of solutions 1, 2 and 3 into 970 ml. of distilled water.

STPP. Sodium tripolyphosphate solution (2.0%) prepared by introducing 20 g. of sodium tripolyphosphate and 10 ml. of each of solutions 1, 2 and 3 into 970 ml. of distilled water with continuous agitation until completely dissolved. The pH of the solution was then adjusted to 8.5+/−0.1 using 0.1N HCl. Any precipitate was allowed to settle but was not removed from the solution.

Sol. 4. 400 ml, distilled water containing 90.3 g of anhydrous sodium acetate diluted to 500 ml. with distilled water.

Sol. 5. 350 ml. distilled water containing 150 g of glacial acetic acid.

Sol. 6. 47.5 ml. of distilled water containing 2.5 ml. of polysorbate 80.

TCA The trichloroacetic acid (TCA) reagent was prepared by mixing 18 g. of TCA with 100 ml. of each of Solutions 4 and 5 and 4 ml. of Solution 6. The resulting solution was then diluted to one liter with distilled water.

THAM 400 ml. of STW containing 18.17 g. of trishydroxy-methyl amino methane.

A casein-containing solution is then prepared by adding, under constant agitation, 6.67 g. (moisture free basis) of Hammerstein casein (purified high nitrogen, marketed by ICN Nutritional Biochemical) to 350 ml. of the STW solution. Stirring is then continued for ten minutes. 50 ml. of THAM solution is then added and stirring is again continued for 10 minutes. The resulting solution is then allowed to equilibrate in a water bath having a temperature of 40+/−0.1 degrees C. for 30 minutes. The pH of the solution then adjusted to 8.5+/−0.1 at 40 degrees C. with 1N NaOH. The solution is allowed to cool to room temperature. It is then diluted to 500 ml. with STW solution. It should be noted that this solution must be prepared daily.

An enzyme-containing solution is then prepared in the STPP solution such that one ml. of the final dilution will have an activity of 20–40 DAPU/ml. The pH of the final dilution is adjusted to 8.5 using either 1N HCL or 1N NaOH.

A 5 ml. sample of the enzyme-containing solution is then transferred to a 25×150 mm. test tube and placed in a constant temperature water bath maintained at 40 degrees C. 5 ml. portions of the casein substrate are then pipetted into each of three 25×150 mm test tubes, one of which is used as a standard for comparative purposes. These samples are then placed in the water bath and allowed to equilibrate at 40 degrees C. for 10 minutes.

Noting the exact time, 1 ml. of the enzyme solution is then introduced into two of the substrate-containing test tubes which are then stoppered. After exactly 40 minutes, 5 ml. of TCA solution is added to each tube and mixed by gentle swirling of the contents.

An enzyme blank is then prepared by adding 5 ml. of TCA solution into the remaining substrate-containing test tube and mixing its contents by gentle swirling.

All test tubes are then placed in the water bath and incubated for 30 minutes. After exactly 30 minutes have passed, the test tubes are transferred to an ice bath where they are allowed to remain for about 5 minutes. The tubes are then centrifuged at about 3000 rpm for about 15 minutes. The supernatant is then recovered into clean cuvettes. The absorbancy of UV radiation (275 nm) by each sample is recorded.

The absorbancy data is then used to calculate the activity of the enzyme through the formula set forth immediately below.

$$DAPU/g = A \times 11/0.00552 \times 40 \times W$$

wherein A is absorbancy difference between the enzyme/substrate sample and the enzyme blank, 11 is the final reaction volume, 0.00552 is the absorbancy of 4 nanomoles of tyrosine, 40 is the elapsed time in minutes and W is the weight in grams added to the reaction mixture in one 1 ml. aliquot.

Through use of the method described immediately above, it was determined that the alkaline protease solution used in the experiments which follow possessed an activity of about 396,800 DAPU/kg, or about 90.2% of its claimed activity.

EXAMPLE 1

A two-phase aqueous system was formulated in a separatory funnel through the addition of (a) 8.0 grams of a 50% aqueous solution of polyethylene glycol having an average molecular weight of about 1450 (manufactured by Union Carbide Corporation and marketed under the tradename of Carbowax (Tm) polyethylene glycol 1450) and (b) 10.0 grams of a 15% aqueous solution of sodium sulfate. To the system was added 1.0 grams of Solution A.

The solution was then diluted with distilled water to a final weight of 20.0 grams and its pH was adjusted to a pH of 4 through the addition of HCl.

The system therefore had the following composition:
20.0% polyethylene glycol
7.5% sodium sulfate
0.009% alkaline protease
balance water The system was agitated and then allowed to separate at room temperature. The phases were when isolated and adjusted to a pH of 8 to allow for a proper comparison with the activity of the control.

The system was found to possess a partition coefficient with respect to alkaline protease of 9.82.

EXAMPLE 2

The system of Example 1 was duplicated except that 1 gram of a 0.2% aqueous solution of polyacrylic acid having an average molecular weight of about 150,000 (manufactured by Polyscience Inc.) was added. The solution therefore contained 0.01% polyacrylic acid.

The system was found to possess a partition coefficient with respect to alkaline protease of 3.75.

EXAMPLE 3

The system of Example 2 was duplicated except that 1 gram of a 2.0% aqueous solution of polyacrylic acid having an average molecular weight of about 150,000 (manufactured by Polyscience Inc.) was added. The solution therefore contained 0.1% polyacrylic acid.

The system was found to possess a partition coefficient with respect to alkaline protease of 16.0.

EXAMPLE 4

The system of Example 1 was duplicated except that the pH of the system was adjusted to a pH of 6.

The system was found to possess a partition coefficient with respect to alkaline protease of 59.0.

EXAMPLE 5

The system of Example 2 was duplicated except that the pH of the solution was increased to a pH of 6. The solution therefore contained 0.01% polyacrylic acid.

The system was found to possess a partition coefficient with respect to alkaline protease of 33.3.

EXAMPLE 6

The system of Example 3 was duplicated except that the pH of the solution was increased to a pH of 6. The solution therefore contained 0.1% polyacrylic acid.

The system was found to possess a partition coefficient with respect to alkaline protease approaching infinity as no absorbance in the lower phase occurred. The absence of the protease in the lower phase was confirmed through mass balance calculations.

EXAMPLE 7

The system of Example 1 was duplicated except that the pH of the solution was increased to a pH of 8.

The system was found to possess a partition coefficient with respect to alkaline protease of 23.2.

EXAMPLE 8

The system of Example 2 was duplicated except that the pH of the solution was increased to a pH of 8. The solution therefore contained 0.01% polyacrylic acid.

The system was found to possess a partition coefficient with respect to alkaline protease of 19.4.

EXAMPLE 9

The system of Example 3 was duplicated except that the pH of the solution was increased to a pH of 8. The solution therefore contained 0.1% polyacrylic acid.

The system was found to possess a partition coefficient with respect to alkaline protease approaching infinity as no absorbance in the lower phase occurred. The absence of the protease in the lower phase was confirmed through mass balance calculations.

EXAMPLE 10

The system of Example 6 was duplicated except that the polyacrylic acid was replaced with polyvinyl sulfonate. The system therefore had the following composition 20.0% polyethylene glycol
7.5 sodium sulfate
0.009% alkaline protease
0.1% polyvinyl sulfonate
pH=6

The system was found to possess a partition coefficient with respect to alkaline protease approaching infinity. This was confirmed through mass balance calculations.

EXAMPLE 11

The system of Example 10 was duplicated except that the polyvinyl sulfonate was replaced with sodium dodecylsulfate.

The system was again found to possess a partition coefficient with respect to alkaline protease approaching infinity.

EXAMPLE 12

The system of Example 4 was duplicated except that the polyethylene glycol was replaced with an equal amount of a methoxy-capped polyethylene glycol having an average molecular weight of about 2,000, (manufactured by Union Carbide Corporation and marketed under the tradename MPEG 2000).

The system was found to possess a partition coefficient with respect to alkaline protease of 25.2.

EXAMPLE 13

The system of Example 12 was duplicated except that 0.1% of the polyacrylic acid employed in Example 3 was added.

The system was found to possess a partition coefficient with respect to alkaline protease approaching infinity.

It can therefore be readily seen that through the practice of the instant invention, one can greatly increase the partition coefficient of a given two-phase aqueous system. Moreover, the potency of the enzyme recovered therefrom appears not to have been deleteriously effected. Furthermore, it has been also been demonstrated that the enzyme may be readily recovered from the enzyme-rich phase through, for instance, the simple addition of additional amounts of the compound to form an insoluble precipitate which then may be isolated.

EXAMPLE 14

The system of Example 1 was duplicated except that 1 gram of a 2.0% aqueous solution of polyvinyl sulfonate was added. The system therefore contained 0.1% polyvinyl sulfonate. The system further possessed a pH of 6.

The partition coefficient of the system with respect to alkaline protease was found to approach infinity as no absorbance in the lower phase occurred. The absence of protease in the lower phase was confirmed through mass balance calculations.

EXAMPLE 15

The system of Example 1 was duplicated except that 1 gram of a 2.0% aqueous solution of sodium dodecylsulfate (SDS) was added. The system therefore contained 0.1% of SDS. The pH of the system was 6.

The system was found to possess a partition coefficient with respect to alkaline protease of 8.4.

What is claimed is:

1. A method for increasing the partition coefficient in an enzyme-containing aqueous bi-phase system wherein said bi-phase system comprises polyethylene glycol, said method comprising providing said system with a compound selected from the group consisting of polyacids, salts of polyacids, carboxymethyl cellulose and the copolymer of maleic anhydride and vinyl ether, said compounds being provided in quantities sufficient to increase the partition coefficient of said enzyme within said system.

2. The method of claim 1 wherein said polyacids are selected from the group consisting of polyacrylic acid, polyvinyl sulfonic acid, polyvinyl sulfonic acid, polyphosphoric acid and polymethacrylic acid.

3. The method of claim 1 wherein said salts of polyacids are selected from the group consisting of the alkali metal salts of polyacrylic acid, polyvinyl sulfonic acid, polyvinyl sulfuric acid, polyphosphoric acid and polymethacrylic acid.

4. The method of claim 1 wherein the enzyme comprises alkaline protease.

5. The method of claim 1 wherein the compound is polyacrylic acid.

6. The method of claim 5 wherein polyacrylic acid is present in a concentration of about 0.0001 to 0.2 wt. % based upon the weight of the total system.

7. The method of claim 5 wherein polyacrylic acid is present in a concentration of from about 0.01 to about 0.1 wt. % based upon the weight of the total system.

8. The method of claim 5 wherein the polyacrylic acid has an average molecular weight of from about 1,000 to about 1.000,000.

9. The method of claim 5 wherein the polyacrylic acid has an average molecular weight of about 150,000.

10. The method of claim 1 further comprising adjusting the pH of the system to maximize the partition coefficient.

11. The method of claim 10 wherein the compound is polyacrylic acid and the pH of the system is between about 4 and about 10.

12. The method of claim 10 wherein the compound is polyacrylic acid and the pH of the system is between about 5 and about 8.

13. The method of claim 1 wherein the aqueous system comprises polyethylene glycol and a water soluble, inorganic salt.

14. The method of claim 13 wherein the water soluble, inorganic salt is selected from the group consisting of magnesium sulfate, potassium sulfate, sodium sulfate and ammonium sulfate.

15. The method of claim 13 wherein the inorganic salt is present in a concentration of from about 1 to 40 wt. % based upon the weight of the total system.

16. The method of claim 13 wherein the organic salt is present in a concentration of from about 5 to 25 wt. % based upon the weight of the total system.

17. The method of claim 13 wherein the polyethylene glycol has an average molecular weight of from about 1,000 to about 10,000.

18. The method of claim 13 wherein the polyethylene glycol has an average molecular weight of about 1,450.

19. A method for increasing the partition coefficient in a two-phase aqueous polyethylene glycol/sodium sulfate system containing alkaline protease comprising;

(a) introducing between 0.01 and 0.1 wt. % of polyacrylic acid into the system;

(b) agitating the system; and (c) allowing the system to establish distinct phases.

20. A method for increasing the partition coefficient in an enzyme-containing aqueous bi-phase system wherein said bi-phase system comprises polyethylene glycol, said method comprising:

(a) introducing into said system a compound selected from the group consisting of polyacids, salts of polyacids, carboxymethyl cellulose and the copolymer of maleic anhydride and vinyl ether, said compound being introduced in quantities sufficient to increase the partition coefficient of said enzyme within said system;

(b) agitating said system;

(c) allowing the system to establish distinct phases;

(d) isolating the phase in which the enzyme is concentrated;

(e) introducing into said isolated phase additional quantities of said compound in sufficient quantities to cause the formation of an insoluble, enzyme-containing precipitate; and (f) isolating the precipitate.

21. The method of claim 20 wherein said polyacids are selected from the group consisting of polyacrylic acid, polyvinyl sulfonic acid, polyvinyl sulfuric acid, polyphosphoric acid and polymethacrylic acid.

22. The method of claim 20 wherein said salts of polyacids are selected from the group consisting of the alkali metal salts of polyacrylic acid, polyvinyl sulfonic acid, polyvinyl sulfuric acid, polyphosphoric acid and polymethacrylic acid.

23. The method of claim 20 wherein the system comprises polyethylene glycol and a water-soluble, inorganic salt.

24. The method of claim 23 wherein the inorganic salt is selected from the group consisting of magnesium sulfate, potassium sulfate, sodium sulfate and ammonium sulfate.

25. The method of claim 23 wherein the inorganic salt is present in a concentration of from about 1 to 40 wt. % based upon the weight of the total system.

26. The method of claim 23 wherein the inorganic salt is present in a concentration of from about 5 to 25 wt. % based upon the weight of the total system.

27. The method of claim 23 wherein the polyethylene glycol has an average molecular weight of from about 1,000 to about 10,000.

28. The method of claim 23 wherein the polyethylene glycol has an average molecular weight of about 1,450 and the water soluble, inorganic salt is sodium sulfate which is present in a concentration of about 7 to about 8 wt. % based upon the weight of the total system.

29. The method of claim 20 wherein the organo-compatible compound is polyacrylic acid.

30. The method of claim 29 wherein polyacrylic acid introduced in step (a) in a concentration of about 0.01 to about 0.1 wt. % based upon the weight of the total system.

31. The method of claim 29 wherein the polyacrylic acid has an average molecular weight of from about 1,000 to about 1,000,000.

32. The method of claim 29 wherein the polyacrylic acid has an average molecular weight of about 150,000.

33. The method of claim 29 wherein the polyacrylic acid introduced in step (e) produces a final concentration of polyacrylic acid in the system of up to about 10 wt. % based upon the weight of the total system.

34. The method of claim 29 wherein polyacrylic acid introduced in step (e) produces a final concentration of polyacrylic acid in the system of from about 2 to about 5 wt. % based upon the weight of the total system.

35. The method of claim 23 further comprising adjusting the pH of the system prior to step (d) to maximize the partition coefficient.

36. The method of claim 35 wherein the additional compound is polyacrylic acid and the pH of the system is between about 5 and about 8.

* * * * *